United States Patent
Ottoboni et al.

(10) Patent No.: US 6,776,761 B2
(45) Date of Patent: Aug. 17, 2004

(54) HOLLOW MICROSPHERES WITH CONTROLLED FRAGILITY FOR MEDICAL USE

(75) Inventors: Thomas B. Ottoboni, Belmont, CA (US); E. Glenn Tickner, Watsonville, CA (US); Robert E. Short, Los Gatos, CA (US); Ronald K. Yamamoto, San Francisco, CA (US)

(73) Assignee: Point Biomedical Corporation, San Carlos, CA (US)

( * ) Notice: Subject to any disclaimer, the term of this patent is extended or adjusted under 35 U.S.C. 154(b) by 0 days.

(21) Appl. No.: 10/225,252

(22) Filed: Aug. 20, 2002

(65) Prior Publication Data

US 2003/0036697 A1 Feb. 20, 2003

Related U.S. Application Data

(63) Continuation-in-part of application No. 09/638,167, filed on Aug. 11, 2000.
(60) Provisional application No. 60/148,947, filed on Aug. 13, 1999.

(51) Int. Cl.[7] .................................................. A61B 8/14
(52) U.S. Cl. ...................... 600/458; 600/437; 600/454; 424/9.51; 424/9.52
(58) Field of Search ................................ 600/437–472; 424/9.51–9.52, 9.5, 450

(56) References Cited

U.S. PATENT DOCUMENTS

| | | | |
|---|---|---|---|
| 3,743,604 A | | 7/1973 | Schnoring et al. |
| 4,681,119 A | * | 7/1987 | Rasor et al. ............... 424/9.52 |
| 4,718,433 A | | 1/1988 | Feinstein |
| 5,041,292 A | | 8/1991 | Feijen |
| 5,271,961 A | | 12/1993 | Mathiowitz et al. |
| 5,310,540 A | | 5/1994 | Giddey et al. |
| 5,501,863 A | | 3/1996 | Rossling et al. |
| 5,518,709 A | | 5/1996 | Sutton et al. |
| 5,562,893 A | | 10/1996 | Lohrmann et al. |
| 5,565,215 A | | 10/1996 | Gref |
| 5,569,468 A | | 10/1996 | Modi |
| 5,585,112 A | | 12/1996 | Unger et al. |
| 5,611,344 A | | 3/1997 | Bernstein et al. |
| 5,620,883 A | | 4/1997 | Shao et al. |
| 5,650,156 A | | 7/1997 | Grinstaff et al. |
| 5,679,377 A | | 10/1997 | Bernstein et al. |
| 5,711,933 A | | 1/1998 | Bichon et al. |
| 5,798,091 A | * | 8/1998 | Trevino et al. ............ 424/9.52 |

(List continued on next page.)

FOREIGN PATENT DOCUMENTS

| | | |
|---|---|---|
| EP | 0 224 934 B1 | 6/1987 |
| EP | 0 398 935 B1 | 11/1990 |
| EP | 0 523 183 B1 | 4/1991 |
| EP | 0 441 468 B1 | 8/1991 |
| EP | 0 458 745 A1 | 11/1991 |

(List continued on next page.)

OTHER PUBLICATIONS

PCT Search Report dated Nov. 14, 2000 in foreign counterpart application PCT/US00/22098.

*Primary Examiner*—Dennis Ruhl
*Assistant Examiner*—William C. Jung
(74) *Attorney, Agent, or Firm*—Dorsey & Whitney LLP (57) ABSTRACT

A composition for ultrasonic imaging is described having a microbubble population of controlled fragility. The microbubbles comprise an outer shell and a hollow core. The ratio of shell thickness to microbubble diameter is substantially similar across the population of microbubbles. A method of using such composition for imaging a fluid filled cavity, vessel or tissue is described.

27 Claims, 3 Drawing Sheets

Fragility Slope for Blended Agent Showing the Two Extremes of the Blend

U.S. PATENT DOCUMENTS

| | | | |
|---|---|---|---|
| 5,830,435 A | 11/1998 | Yan et al. | |
| 5,837,221 A | 11/1998 | Bernstein et al. | |
| 5,840,275 A | 11/1998 | Bichon et al. | |
| 5,863,520 A | 1/1999 | Bichon et al. | |
| 5,919,434 A | 7/1999 | Dugstad et al. | |
| 5,922,304 A | 7/1999 | Unger | |
| 5,948,387 A | 9/1999 | Unger | |
| 5,957,848 A * | 9/1999 | Sutton et al. | 600/458 |
| 6,017,310 A * | 1/2000 | Johnson et al. | 600/458 |
| 6,028,066 A | 2/2000 | Unger | |
| 6,120,805 A | 9/2000 | Spenlehauer | |
| 6,171,246 B1 * | 1/2001 | Averkiou et al. | 600/458 |
| 6,193,951 B1 | 2/2001 | Ottonobi | |
| 6,207,135 B1 | 3/2001 | Rossling et al. | |
| 6,224,554 B1 | 5/2001 | Tickner | |
| 6,319,204 B1 * | 11/2001 | Brock-Fisher et al. | 600/458 |
| 6,340,348 B1 * | 1/2002 | Krishnan et al. | 600/447 |
| 6,425,869 B1 * | 7/2002 | Rafter et al. | 600/458 |
| 2001/0012522 A1 * | 8/2001 | Ottoboni et al. | 424/501 |
| 2002/0151792 A1 * | 10/2002 | Conston et al. | 600/439 |

FOREIGN PATENT DOCUMENTS

| | | |
|---|---|---|
| EP | 0 512 593 A1 | 11/1992 |
| EP | 0 681 843 A2 | 11/1995 |
| GB | 2 256 183 B | 12/1992 |
| WO | WO 91/12823 | 9/1991 |
| WO | WO 92/18164 | 10/1992 |
| WO | WO98/48783 | 11/1998 |
| WO | WO 99/00149 | 1/1999 |
| WO | WO 99/39697 | 8/1999 |
| WO | WO00/12062 | 3/2000 |
| WO | WO00/527792 | 10/2000 |
| WO | WO01/12069 | 2/2002 |
| WO | WO01/12071 | 2/2002 |
| WO | WO03/034975 | 5/2003 |

* cited by examiner

Figure 1. Mean Backscatter AD along Flow Phantom for Agent M985 @ MI=1.6

Figure 2. Fragility Slope for Agent M1001 as a Function of Intensity Showing the Critical MI Figure 3. Fragility Slope for Blended Agent Showing the Two Extremes of the Blend

HOLLOW MICROSPHERES WITH CONTROLLED FRAGILITY FOR MEDICAL USE

FIELD OF INVENTION

This is a continuation-in-part of Ser. No. 09/638,167, now abandoned filed Aug. 11, 2000, in which the priority of Provisional Application Serial No. 60/148,947, filed Aug. 13, 1999, is claimed. The disclosures of said applications are incorporated by reference herein.

This invention relates to a method of enhancing diagnostic use of ultrasound by providing a microbubble contrast agent having a controlled fragility. Specific use of the methodology involves the enhancement of tissue perfusion imaging, measurement of physiological pressure, and delivery of drugs.

BACKGROUND OF INVENTION

It is well known that microbubbles are efficient backscatterers of ultrasonic energy. Thus, microbubbles injected interstitially or into the bloodstream can enhance ultrasonic echographic imaging to aid in the visualization of biological structures such as the internal organs or the cardiovascular system. Contrast is achieved when acoustic impedance between two materials at an interface is different. Thus, the greater the impedance difference between the two materials the greater the intensity of the ultrasound echo. Since there is a large difference between the acoustic impedance of body tissue and gas, microbubbles offer excellent ultrasound contrast to aid in delineating biological structures that otherwise would be difficult to distinguish.

Over the past few years, a variety of methods have been developed for the manufacture of ultrasonic contrast agents. The processes for their fabrication usually involve spray drying, emulsion, or interfacial polymerization techniques. Typically, the result is a microbubble population having a range of diameters with either a fixed or an arbitrarily variable wall thickness. An ultrasonic contrast agent produced by one methodology, for example, may contain microbubbles where each has a shell wall of the same thickness regardless of its diameter. Alternatively, a different method of production may result in a microbubble population with wall thickness varying even between those microbubbles having the same diameter.

For many applications, a microbubble contrast agent with the aforementioned characteristics may not be optimal. For example, of major interest is the use of microbubbles administered intravenously to provide echographic contrast to the blood pool for enhanced imaging of the vascularized organs and structures, especially the heart. Hydrostatic pressures of the cardiovascular system can in many cases approach 250 mmHg. At such pressures, microbubbles within the population having relatively thinner walls could be subject to rupture and loss of internal gas. If this occurs before the agent reaches the imaging region, then the result is a degradation of contrast performance.

Further, an important aspect of imaging the cardiovascular system is the measurement of blood perfusion through the tissues of the heart. This is best accomplished by a procedure wherein systemically introduced microbubble agent is first cleared from a region of interest by exposure with an insonating signal having a power intensity sufficiently high to rupture and thus destroy the microbubbles that are present in the field. Reflow of agent into the region is then recorded using a relatively lower ultrasound power setting where the microbubbles are no longer being destroyed. In this case, microbubbles within the population having thicker walls may be so durable that they survive the high intensity ultrasound beam. Efficacy is reduced due to the residual contrast resulting from the remaining undamaged microbubbles still present in the imaging region.

Another application for which microbubbles having an arbitrary wall thickness may be unsuitable is in the field of ultrasonically mediated drug delivery. Conceptually, a microbubble agent is, through processing, internally loaded with a drug. The treated microbubbles are then injected intravenously and allowed to systemically circulate. An ultrasound signal of sufficient energy to rupture the drug containing microbubbles is applied to a region where the delivery of the drug is desired. The insonating beam destroys the microbubbles and thus releases its payload. However, a microbubble population having an arbitrary wall thickness could result in the drug being released prematurely or not at all. Those with thinner more fragile walls may rupture from hydrostatic pressure before reaching the site. Those with thicker more durable walls may not rupture at all.

A microbubble population with a fixed wall thickness but having a range of diameters would similarly be unsuitable for these applications. While the strength of a microbubble is a function of the thickness of its wall, it is also a function of its diameter. Thus, a relatively smaller microbubble would show more resistance to hydrostatic and acoustic pressures than would a relatively larger bubble having the same wall thickness.

A microbubble agent having a controlled fragility would therefore represent an improvement to the state of the art. For purposes here, the term "controlled fragility" is taken to describe a microbubble population having the characteristic of being rupturable only when exposed to acoustic energy equal to or greater than a predetermined intensity. That is, below this acoustic intensity threshold, substantially all the microbubbles remain intact while above the acoustic intensity threshold the microbubbles rupture. Thus, the agent can be turned-on or turned-off by controlling the intensity of the insonating signal.

An ultrasonic contrast agent having a controlled fragility characteristic would be of benefit to blood profusion studies. After systemic injection, the agent would perfuse into the tissues of interest where it would provide image contrast. Acoustic intensity could then be increased above a predetermined value in order to rupture those microbubbles in the field. The ruptured microbubbles release the gas encapsulated within and the gas in turn quickly dissolves. The region would then be essentially devoid of contrast. The intensity could once again be reduced so that an image can be continuously recorded as a fresh supply of microbubbles from the systemic blood pool flowed into the region. Alternatively, when ultrasound modalities which rely on microbubble destruction to generate contrast, intermittent imaging at intensities designed to rupture the microbubbles may be used to monitor reperfusion of blood into the region.

Likewise, drug-containing microbubbles having a controlled fragility would provide increased efficacy because microbubble rupture, and hence, release of their contents would occur only at the region where the intensity of acoustic energy is greater than that needed for microbubble rupture.

If the ultrasound imaging agent is to be used in blood pool applications, it is preferred that the majority of the microbubbles have diameters within the range of about 1 to 10 microns. This will insure that the microbubbles are small enough to pass through the capillary system unimpeded.

A variety of ultrasound imaging modalities are available for use with echographic contrast agents. Among these modalities are B-mode (both fundamental and harmonic), power doppler, and pulse inversion imaging. Each is typically best suited to specific applications. Of those applications described above, one modality or another may be most suitable to use in concert with a microbubble agent having a controlled fragility. For example, power doppler techniques has been shown to provide good results for imaging myocardial perfusion when using high MI intermittent imaging techniques. Pulse inversion methods, on the other hand, are most suitable when low MI continuous mode imaging is used to monitor perfusion. A more detailed description of the different echographic imaging modalities can be found in the *Handbook of Contrast Echocardiology* by H. Becher et. al. (Becher, Harold and Peter N. Burns; *Handbook of Contrast Echocardiography*; 150 pp, 100 figures; (2000).)

A microbubble population having a controlled fragility is most useful as an ultrasound imaging agent when the microbubbles of the population are rupturable within a power range typical of diagnostic imaging. This range is typically what is required to produce a field having a Mechanical Index from about 0.1 to about 2.6.

It is an object of the present invention to provide an ultrasound contrast agent consisting of a microbubble population having a controlled fragility. Also provided is a method for echographic enhancement using a microbubble contrast agent having controlled fragility.

SUMMARY OF THE INVENTION

An ultrasound imaging agent composition is provided consisting of a microbubble population having a controlled fragility wherein the wall thickness of the outer shell of each microbubble forms a ratio with the microbubble diameter that is substantially the same as the wall thickness to diameter ratio of all other microbubbles in the population.

Methods of producing such a microbubble imaging agent composition incorporate emulsification techniques wherein the emulsion droplets formed in the process are microbubble precursors with each containing equal concentration of wall-forming material irrespective of droplet diameter. Thus, a larger droplet would contain wall-forming material that is greater in amount than a smaller droplet by a ratio that provides for a wall thickness that is linearly related to diameter. An ultrasound imaging agent so produced would contain microbubbles exhibiting equivalent resistance to the hydrostatic and acoustic stresses present in the ultrasound imaging field.

A method of echographic imaging using such an ultrasound imaging agent composition within a fluid-filled cavity, vessel or tissue comprises the steps of:

a. introducing a microbubble contrast agent consisting of a microbubble population having a constant wall thickness to diameter ratio that is characterized by a threshold intensity of ultrasonic power of microbubble rupture that is within the power range useful for diagnostic imaging, into said region of interest;

b. applying an ultrasonic signal to said region of interest at an applied power intensity greater than the threshold intensity;

The signal generated by the destruction of the microbubbles can also be ultrasonically recorded. The applied power intensity may also be reduced to less than the threshold intensity. Then the reflow of the microbubble agent into the region of interest can be measured.

DETAILED DESCRIPTION OF THE INVENTION

A method for increasing the efficacy of an echographic microbubble contrast agent is to produce a microbubble population having a controlled fragility derived from a specific relationship between the microbubble wall and its diameter. This relationship requires that, irrespective of diameter, the microbubbles exhibit an equivalent resistance to the acoustic and hydrostatic stresses associated with an echographic imaging environment.

As used herein, the term microbubble is intended to describe a particle which is between about 1 and 1000 microns in diameter, is roughly spherical, and is composed of an outer shell enclosing a hollow core filled with a gas.

It can be shown mathematically that the strength, that is resistance to a hoop stress, of a thin-walled hollow sphere is a function of the diameter of the sphere and the thickness of its wall. Further, this relationship is linearly proportional with diameter and inversely proportional with thickness. Thus, for a given applied pressure, if the ratio of thickness to diameter is constant, then the hoop stress on the sphere wall remains constant irrespective of diameter.

An ultrasonic contrast agent consisting of a spectrum of microbubbles all having the same wall thickness to diameter ratio would therefore exhibit essentially an equivalent resistance to the stresses imparted by the hydrostatic and acoustic forces present in the ultrasonic imaging environment.

The maximum wall stress in a pressurized sphere has been solved by Timoshenko and Goodier. (Timoshenko, S. and J. N. Goodier; "Theory of Elasticity"; McGraw-Hill Book Company, New York, N.Y.; (1951): 356–359.) The authors find that the hoop stress, $\sigma_\theta$, for an elastic homogeneous material is given by:

$$\sigma_\theta = (P/2)(2a^3+b^3)/(b^3-a^3) \quad (1)$$

where a is the inner radius, b is the outer radius, and

P is the pressure difference across the wall.

If we assume that wall thickness, h, is very thin, then equation 1 simplifies to:

$$\sigma_\theta = (P/2)(R+h)/h \quad (2)$$

where R is the mean radius.

If the wall thickness, h, is thin compared to mean radius, R, that is R>>h, equation 2 can be further simplified:

$$\sigma_\theta = (P/2)(R/h) \quad (3)$$

Rewriting this expression in terms of the diameter, d, we obtain $$\sigma_\theta = (P/4)(d/h) \quad (4)$$

The hoop stress for all elastic materials has a limit above which the material will fail. It is a physical constant. Letting this value be identified as $\sigma_{\theta\text{-}max}$ and the corresponding pressure causing the failure identified as $P_{max}$ and rewriting equation 4, we obtain:

$$P_{max}=4\sigma_\theta(h/d) \quad (5)$$

Thus, it can be noted from equation 5 that the maximum allowable pressure, $P_{max}$, is also a constant so long as the wall thickness-diameter ratio (h/d) remains constant. It becomes a property of the microbubble. If there were a spectral distribution of bubble diameters but all possessed the same h/d ratio, all microbubbles would begin to fail at the same time. In contrast, if the h/d ratio varies, then there, is a range of pressures which would cause agent failure. Clearly, a sharp definitive cutoff provides a number of advantages.

The mechanical, index (MI) identified on ultrasound scanners is a measure of the maximal rarefactional (negative) pressure in the propagated ultrasound field. If the MI were increased systematically from a transducer focused on a plethora of microbubbles possessing a constant h/d ratio, there would be no breakage until the rarefactional pressure of $P_{max}$ was reached. The value of MI when this event is achieved is referred to as the critical MI ($MI_{crit}$). Microbubbles continue to break for all values above this value of $MI_{crit}$. However, the rate of destruction increases as the power level rises. If the h/d ratio is not constant, then there is not a clean initiation of agent destruction. Failure begins at near zero MI and the rate of destruction increases thereafter. Thus, there is no critical MI, there is no controlled fragility.

A microbubble population having a constant diameter to wall thickness ratio can be produced by an emulsion solvent evaporation process. First, two solutions are prepared. One is an aqueous solution containing an appropriate surfactant material which may be an amphiphilic biopolymer such as gelatin or albumin. Viscosity enhancers may additionally be included. This becomes the outer continuous phase of the emulsion system. The second is made from the dissolution of a wall-forming polymer in a mixture of two water immiscible organic liquids. The polymer which forms the inner wall may be a biodegradable synthetic polymer such as a polycaprolactone, polylactide, polyglycolide, polyhydroxyvalerate, polyhydrobutrate, or copolymers of the polymers; or natural polymer such as a protein. Useful proteins include collagen, gelatin, albumin, and globulin. One of the organic liquids is a relatively volatile solvent for the polymer and the other is a relatively non-volatile non-solvent for the polymer. The relatively non-volatile non-solvent is typically a C6–C20 hydrocarbon such as decane, undecane, cyclohexane, cyclooctane and the like. The relatively volatile solvent is typically a C5–C7 ester such as isopropyl acetate. Other polymer solvents, methylene chloride for example, may be used so long as they are miscible with the accompanying non-solvent.

The polymer solution (inner organic phase) is added to the aqueous solution (outer phase) with agitation to form an emulsion. A variety of devices can be used to produce the emulsion, e.g. colloid mills, rotor/stator homogenizers, high pressure homogenizers, and ultrasonic homogenizers. The emulsification step is carried out until the inner phase droplets are of the desired size spectrum. It is this-droplet size that will determine the approximate size of the microbubble.

The emulsion thus produced may optionally be further diluted into a water bath with moderate mixing. Mixing is continued while maintaining a bath temperature appropriate for the relatively volatile solvent to evaporate while the relatively non-volatile non-solvent remains. As the solvent volatilizes, polymer concentration in the droplet increases to point where it precipitates in the presence of the less volatile non-solvent. This process forms a film of polymer at the surface of the emulsion droplet. As the process continues, an outer shell wall is formed which encapsulates an inner core of the non-solvent liquid. Once complete, the resulting microcapsules can then be retrieved and washed. Subsequent drying, preferably by freeze-drying, removes the organic liquid core to form a hollow gas-filled microbubble.

If it is desired to form a bilayered shell having an outer layer of a biologically compatible material over the inner polymer layer, an amphiphilic biopolymer may be used as the emulsion forming surfactant material. Such materials tend to be deposited and adhere to interfaces such as the outer surface of the emulsion droplets. Preferred amphiphilic materials are proteins such as collagen, gelatin, casein, serum albumin, or globulin. Human serum albumin is particularly preferred for its blood compatibility. The deposited amphiphilic material is then stabilized by chemical crosslinking to render a contiguous insoluble layer. Suitable chemical crosslinkers include the aldehydes like formaldehyde and glutaraldehyde or the carbodiimides such as dimethylaminopropyl ethylcarbodiimide hydrochloride.

Microbubbles produced by the general procedures outlined above will be of a size approximate to the emulsion droplets from which they were derived. In such a case, a relationship between the concentration of the wall forming material in the polymer solution, the microbubble diameter, and the wall thickness can be derived.

Defining $v_w$=volume of the microbubble wall, $$v_w=VC/\rho \quad (6)$$

where,

V=volume of the emulsion droplet,

C=mass concentration of wall forming material, and $\rho$=dry density of the wall forming material For d>>h, $$h=v_w/S \quad (7)$$

where S=surface area of the emulsion droplet.

Substituting, $$h=VC/S\rho \quad (8)$$

Since for a sphere, $V=\pi d^3/6$ and $S=\pi d^2$, $$h=C(\pi d^3/6)/\rho(\pi d^2) \quad (9)$$

Simplifying, $$h=Cd/6\rho \quad (10)$$

rearranging, $$h/d=C/6\rho \quad (11)$$

Since C and $\rho$ are constants for a given set of process conditions, it follows that h/d is also constant. A microbubble population having a constant wall thickness to diameter ratio possesses a controlled fragility.

Of the various echographic applications for which a microbubble contrast agent having a controlled fragility would provide benefit, each would likely call for an agent tailored to a specific set of requirements. A microbubble construct optimized for use as a myocardial perfusion agent, for example, may require properties distinctly different from an agent optimized for ultrasonically mediated drug delivery. It may even be desirable to provide for a set of agents all having, for example, the same size spectrum but with a range of fragilities. Such a selection could be useful where patient size and body type could be a factor in the quality of the ultrasonic images. In monitoring myocardial perfusion, for example, an ultrasound image taken from a larger chested patient would suffer from increased signal attenuation compared to that of a smaller chested patient. Thus, a more fragile agent, or one that is destroyed at a lower power intensity, might provide a better quality image than a less fragile agent more optimized for a smaller subject. Typical targets for monitoring or mediated drug delivery are the heart, kidneys and liver.

Adjustment of the controlled fragility property can be achieved in several ways. By manipulating the initial concentration of the wall-forming material in the inner phase solution of the emulsion system, for example, the ratio of h/d can be adjusted to increase or decrease the acoustic intensity threshold at which the microbubble ruptures. Wall material selection can also be used to modify the ultimate wall strength of the microbubble. Those materials having a higher yield stress property would provide for a less fragile microbubble. Average molecular weight of the material may also be manipulated to modify the controlled fragility characteristic as a lower molecular weight material would generally produce a more fragile wall. Use of additives such as plasticizers may also be considered since such additives typically affect the mechanical properties of the material including yield strength.

A multilayered shell can also be made. For example, there can be an outer layer of a biocompatible amphiphilic material to expose a biocompadible surface to the body and an inner structural layer of biodegradable polymer for substantially controlling the fragility. The precise fragility property would be determined by the h/d ratio where h is the thickness of the structural polymer layer. Useful biocompatible amphiphilic outer layers include proteins such as collagen, gelatin, casein, albumin and globulin.

The controlled fragility characteristics of a microbubble agent may be predetermined by a number of ways. One method is to place a test agent in a beaker after first examining the suspension for optical density and then insonating the suspension at progressively higher MI settings until a degradation in optical density is observed. This point will identify the critical MI.

Acoustic densitometric (AD) methods may also be used. One technique utilizes a Doppler flow phantom. The transducer of a scanner is placed in the water well atop the phantom, oriented downwards, and focused on the flow tube. The suspended microbubble agent is pumped through the phantom at constant flow rate and viewed on the scanner. AD measurements are then made from the images. If there is no agent destruction, the AD reading is constant along the length of the flow-tube, as backscatter remains constant therein. The scanner power level is increased and the process is repeated. At some point, the microbubbles will fail and there will be a decrease in AD readings axially along the phantom. This decrease provides two useful pieces of information. The slope of the curve identifies the fragility rate (measured in AD/cm) and is a function of the local MI. The intercept value with the y-axis provides a measurement of the peak backscatter from the test agent. The process is repeated for several power settings and the data collected. Following the tests, the measured fragility slopes are plotted as a function of MI. The intercept of the x-axis (MI) provides the critical MI for the test agent.

Another AD method utilizes a clear chamber placed under water. Microbubble agent is contained within the chamber without flow. An ultrasound transducer is submerged and oriented toward the center of the chamber containing the test agent. As the scanner emits pulses of ultrasound, the backscattered data is collected over time. If there is no agent destruction, the backscattered signal remains constant over time. The power level is increased and the process is repeated. Again at some point, the agent will begin to fail. When this occurs, the backscatter will decrease over time as more and more of the agent is destroyed. The decay time constant is noted and the process continued at a higher, power level. When sufficient data are collected, the decay time constants are plotted against MI. Again, the intercept of the regression fit to the data with the x-axis identifies the critical MI, that is the value of MI required to initiate microbubble destruction.

Analytical means may also be employed to establish the fragility characteristics of the agent. Microbubble wall thickness and diameter can be determined directly by scanning electron or transmission electron microscopy or indirectly from knowledge of the wall material mass density, the microbubble count, and the size histogram. These results may be incorporated into the appropriate equations along with the wall material constants to estimate the acoustic and/or hydrostatic pressures necessary to rupture the microbubbles. Finally, in-vivo procedures using an appropriate animal model may be used to corroborate the in-vitro and analytical results.

These approaches permit the determination of the critical MI which is the primary manifestation of controlled fragility. If the agent does not exhibit a unique characteristic as identified here, the critical MI will be essentially zero. With such an agent, there is no turn-on and turn-off capability, and no controlled fragility.

The following examples are provided by way of illustration but are not intended to limit the invention in any way.

EXAMPLE 1

Preparation of Polylactide Microbubbles having a Constant Wall Thickness to Diameter Ratio A 6% aqueous solution was prepared from a 25% solution of USP grade human serum albumin by dilution with deionized water. The pH of the solution was adjusted to 4 using 1M HCl. Separately, 0.41 gm poly d,l-lactide and 5.63 gm cyclooctane were dissolved in 37.5 gm isopropyl acetate. The organic solution was then slowly incorporated into 25 gm of the prepared albumin solution with mild stirring while the mixture was maintained at 30° C. The resulting coarse o-w emulsion was then circulated through a stainless steel sintered metal filter element having a nominal pore size of 7 microns. Recirculation of the emulsion was continued for 8 minutes. The emulsion was then added with stirring to 350 ml deionized water maintained at 30° C. and containing 1.0 ml of 25% glutaradehyde. During the addition, the pH of the bath was monitored and adjusted as necessary with 1N NaOH to insure that it remained between 7 and 8. Low sheer mixing was continued for approximately 2½ hours until the isopropyl acetate had substantially volatilized. Poloxamer 188 in the amount of 0.75 gm was then dissolved into the bath. The resulting microcapsules were retrieved by centrifugation and washed two times in an aqueous solution of 0.25% poloxamer 188. The washed microcapsule suspension was then formulated in a glycine/polyethylene glycol solution and then lyophilized. The resulting dry white cake was reconstituted with deionized water and examined under the microscope to reveal spherical discrete microbubbles.

EXAMPLE 2

Preparation of Microbubbles having a Constant Wall Thickness to Diameter Ratio

A 25 gm aqueous solution containing 6% human serum albumin (HSA) was prepared by dilution from 25% USP grade HSA. The pH of the solution was adjusted to 4.0 with HCl. Separately, a 42.5 gm polymer solution containing 0.9% poly dl-lactide (0.44 dL/gm in $CHCl_3$ at 30° C.), 12.9% cyclooctane, and 86.2% isopropyl acetate was prepared. The organic solution was slowly incorporated into the prepared aqueous solution using magnetic stirring to form a coarse oil-in-water emulsion. While maintaining a temperature of 30° C., the resulting emulsion was then circulated through a stainless steel sintered metal filter element having a nominal pore size of 7 microns. Recirculation of the emulsion was continued for 10 minutes until the inner phase droplets were less than approximately 10 microns in diameter. The emulsion was added with stirring to 200 ml of a 30° C., 2.5% HSA solution also prepared by dilution from USP grade HSA. The mixture was adjusted to a pH of 7.4 using 1N NaOH. Low sheer mixing was continued for approximately 4 hours until the isopropyl acetate had substantially volatilized. Poloxamer 188 in the amount of 0.5 gm was dissolved into the bath. The microcapsules resulting from the procedure were retrieved by centrifugation and washed two times in an aqueous solution of 0.25% poloxamer 188. The washed microcapsules were suspended in an aqueous medium containing bulking agent and dispersant, dispensed into 10 ml vials, and then lyophilized. A sample vial was retrieved and 2 ml deionized water was added to the vial to reconstitute the dry white cake contained within. Microscopic inspection of the reconstitute revealed a suspension of spherical discrete gas-filled microcapsules.

EXAMPLE 3

Preparation of Microbubbles having a Constant Wall Thickness to Diameter Ratio

A 25 gm aqueous solution was prepared by dissolving 0.25 gm polyvinyl alcohol (87%–89% hydrolyzed, average Mw=45 k–65 k) into deionized water. Separately, a 42.5 gm polymer solution was prepared by dissolving poly dl-lactide (0.44 dL/gm in $CHCl_3$ at 30° C.) at a concentration of 0.9% and cyclooctane at 12.9% into isopropyl acetate. The organic solution was slowly incorporated into the prepared aqueous solution using magnetic stirring to form a coarse oil-in-water emulsion. While maintaining a temperature of 30° C., the resulting emulsion was then circulated through a stainless steel sintered metal filter element having a nominal pore size of 7 microns. Recirculation of the emulsion was continued for 10 minutes until the inner phase droplets were less than approximately 10 microns. The emulsion was diluted into 350 ml of a 30° C. aqueous solution containing 3% mannitol. Low shear mixing was maintained for approximately 3½ hours until the isopropyl acetate had substantially volatilized. Poloxamer 188 in the amount of 0.75 gm was dissolved into the bath. The microcapsules resulting from the procedure were retrieved by centrifugation and washed two times in an aqueous solution of 0.25% poloxamer 188. The washed microcapsules were suspended in an aqueous medium containing bulking agent and dispersant, dispensed into 10 ml vials, and then lyophilized. A sample vial was retrieved and 2 ml deionized water was added to the vial to reconstitute the dry white cake contained within. Microscopic inspection of the reconstitute revealed the presence of discrete gas-filled microcapsules.

EXAMPLE 4

In-vitro Method for Establishing Acoustic Fragility Threshold

A Hewlett Packard 5500 ultrasound scanner was used for this study in conjunction with an ATS Laboratories, Model 524 Doppler Flow Phantom. The S4 transducer was positioned vertically downward and oriented along the centerline of the 6 mm diameter flow tube within the phantom. The tip of the transducer was placed in a water well provided by the manufacturer. The flow tube appeared as a constant diameter tube (dark interior) in the sector of the scan. The scanner was set in the harmonic mode (1.8/3.6 MHz) with a beam width of approximately 4 cm at the 4 cm depth of the tube centerline below the transducer. A peristaltic pump delivered liquid containing test agent from a 500 ml beaker placed on a magnetic mixer through the phantom and into a discharge container. This fluid was not recirculated. The fluid was stirred constantly in the beaker throughout the test.

Microbubble agent prepared in accordance with the procedures in Example 1 was placed in the beaker, thoroughly mixed with degassed water and pumped through the phantom with a mean velocity of almost 1 cm per second. Flow velocity was maintained constant throughout the test. Axial positions were marked on the scanner monitor and measured from the proximal end of the flow tube along the centerline using the caliper function of the system. A circular (11×11) region of interest (ROI) was selected for the study and used exclusively throughout. The interval was set at 200 ms for any acoustic densitometric (AD) measurement made. Power levels could be varied and local AD measurement made for each power setting and each location. The highest mechanical index (MI) that the system was capable of producing with this setup was 1.6. The system provides 60 reading at 200 ms intervals. The average reading was used for each local reading.

Figure 1:
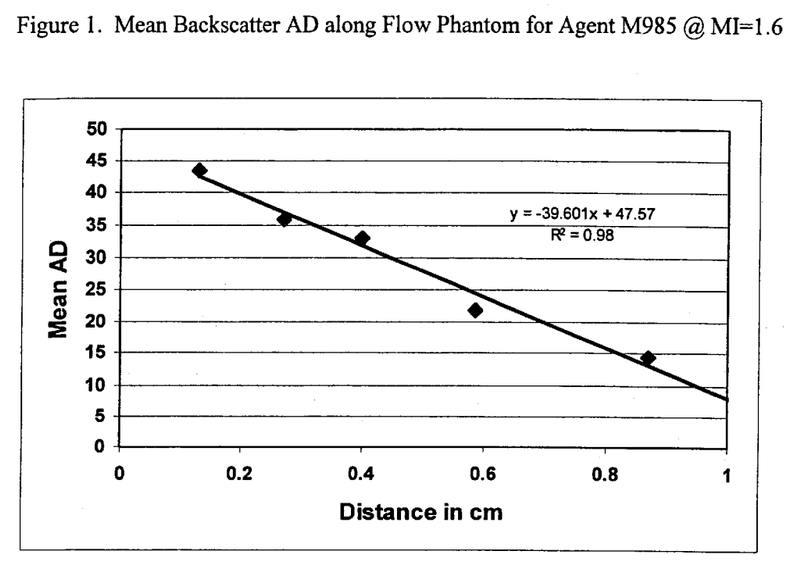
FIG. 1 is a plot of acoustic densitometric measurement vs. distance from the scanner described in Example 4.
Figure 2:
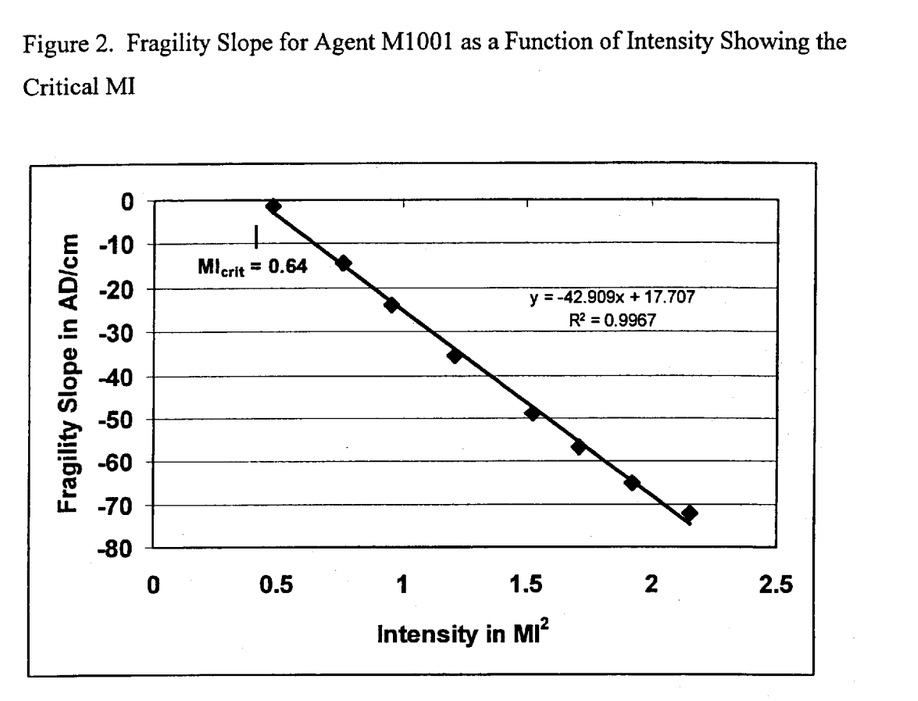
FIG. 2 is a plot of fragility slope vs. signal intensity described in the same experiment.

Using the experimental set-up with the HP 5500 and Doppler Flow Phantom as detailed above, an experiment was performed to determine the fragility threshold of the test agent. If the agent does not rupture, the AD reading is constant along the flow phantom. If the agent does fail, there is a decrease in AD reading along the flow phantom, and there is a slope associated with this decease. This is shown in FIG. 1. A linear regression fit to the data permits the determination of the fragility slope. This slope is plotted against MI as seen in FIG. 2 and this graph permits determination of the point where the agent begins to fail, i.e. slope becomes zero. The value of the MI at this point is the critical MI ($MI_{crit}$). Examination of these results reveals that when the mechanical index exceeds 1 ($MI_{crit}$=1), the agent ruptures. A value below $MI_{crit}$ results in the agent remaining intact.

The test also permits evaluation of the maximal backscatter from the regression fit data in FIG. 1 at zero axial position (47.6 in FIG. 1). This value has been found to depend upon microbubble dosage. Thus, the test permits the determination of both the critical MI whereby the agent begins to fail and the maximal backscatter at the power level tested.

EXAMPLE 5

Figure 3:
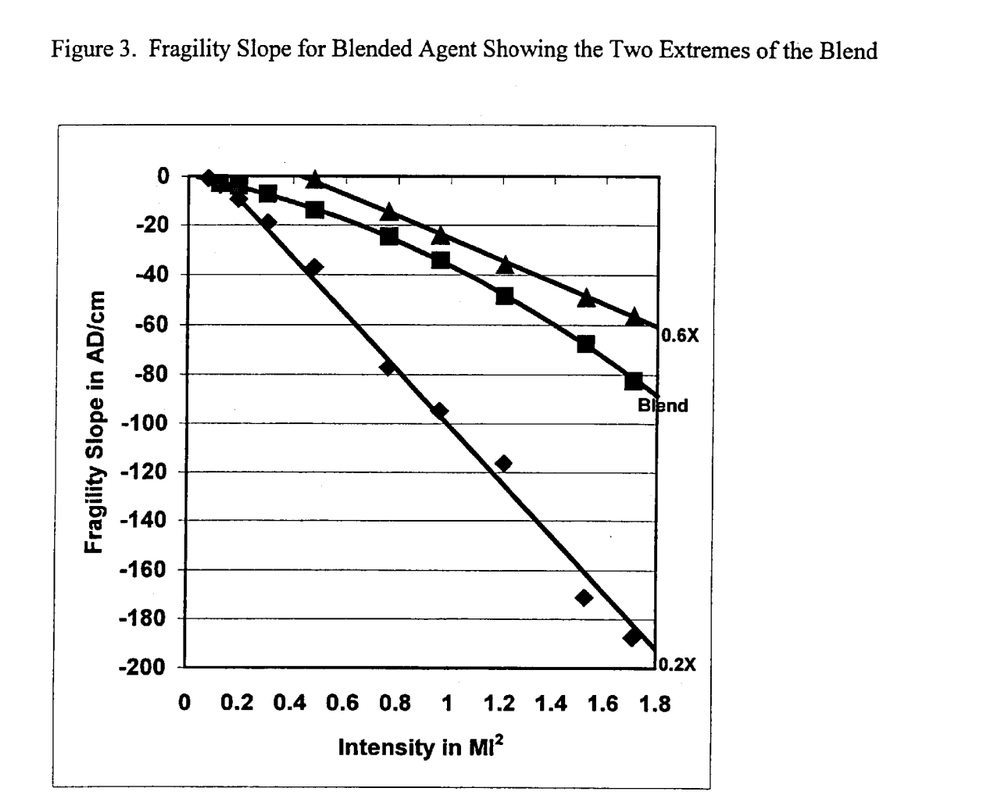
FIG. 3 is a plot of fragility slope vs. intensity described in Example 5.

Comparison of Acoustic Response of Microbubbles having Controlled Fragility with Microbubbles having an Arbitrary Wall Thickness In a comparative study, microbubble agent having an arbitrary wall thickness was tested along with two agents exhibiting controlled fragility. The agent having an arbitrary wall thickness was represented by a mixture of several microbubble populations each prepared by means similar to Example 1 but differing in their wall thickness to diameter ratio. This was achieved by varying the concentration of wall forming material for each prepared batch included in the mixture. All other parameters remained the same, including wall material, mean diameter, and spectral size distribution. The Doppler Flow Phantom and the HP 5500 Scanner were employed for this study according to the procedures described in Example 4. Results are shown in FIG. 3.

Three plots are shown on the graph. Two of the plots are results taken from microbubble agents having constant wall thickness to diameter ratios, one representing a relatively durable microbubble population (identified as "0.6×") and one of a relatively fragile population (identified as "0.2×"). The third plot, identified as "blend", are the results derived from the microbubble agent having a variable wall thickness to diameter ratio and hence having an arbitrary wall thickness.

Upon evaluation of the results of the two agents having constant h/d, it is evident that there is a good linear fit to the data even up the point of intercept with the x-axis. This relationship is typical for agents with constant h/d. The critical MI of an agent is determined by identifying the x-intercept. Using linear regression techniques, the critical MI for the 0.2× and 0.6× microbubble agents are calculated to be 0.36 and 0.64, respectively. Note that the 0.6× agent has a higher critical MI than does the 0.2× microbubble agent. This is an expected result since the 0.6× agent has a greater h/d value and thus is the more durable of the two.

By contrast, the data points taken from the agent having the variable h/d displays neither a linear relationship nor a clearly defined critical MI. The results demonstrate that a microbubble agent having a variable h/d, or synonymously an arbitrary wall thickness, begins to fail almost immediately as those microbubbles in the blend having the thinnest walls would begin to rupture almost immediately. As signal intensity is increased a higher percentage of the agents become involved in the rupture process. Thus, the blended data exhibits a curvilinear relationship indicating the continuous failure of the new material as power is increased. The result is a microbubble agent with no critical MI and hence no controlled fragility.

EXAMPLE 6

Myocardial Profusion Study Using Microbubbles having a Controlled Fragility

For the study, an Agilent SONOS 5500 ultrasound system was operated in its real-time perfusion imaging mode. An anesthetized canine was laid on its right side on top of the ultrasound transducer so that a closed-chest, parasternal short-axis view of the heart could be imaged. The frame rate of the ultrasound system was set to 16 Hz and the output power was set to a mechanical index (MI) of 0.2 for the imaging frames and an MI of 1.0 for the microbubble destruction frame. A microbubble suspension produced in accordance with the procedures of Example 1 was reconstituted in deionized water, diluted, and infused intravenously into a femoral vein. Agent was detected filling first the right ventricular cavity, the left ventricular cavity, and finally the myocardium of the left ventricle. Once the intensity in the myocardium peaked, destruction frames were fired to break the microbubbles in the myocardium. Low-power detection frames followed, allowing one to monitor the myocardial intensity to increase and peak as intact microbubbles re-perfused the myocardial tissue over time. Off-line analysis of the re-perfusion frames selected from the same point in the cardiac cycle showed a steady increase of myocardial intensity over time.

A is a series of ultrasound images were made showing the progression of events described above. In the first frame, microbubbles in the myocardium and left ventricular cavity were seen. In the second frame a high-power frame is used to destroy microbubbles in both the myocardium and cavity. In the third frame, while the low-power pulses continue to show detection of microbubbles in the cavities due to the large blood volume, the myocardium is essentially devoid of agent. In the fourth frame microbubble re-perfusion of the myocardium were seen, similar to the first frame.

What is claimed is:

1. A method of echographic imaging using a microbubble contrast agent in a region of interest within a fluid-filled cavity, vessel, or fluid perfused tissue comprising the steps of:
   a. introducing a microbubble contrast agent consisting of a microbubble population having a constant wall thickness to diameter ratio that is characterized by a threshold intensity of ultrasonic power of microbubble rupture that is within the power range useful for diagnostic imaging into said region of interest,
   b. applying an ultrasonic signal to said region of interest at an applied power intensity greater than said threshold intensity.

2. A method according to claim 1 comprising the further steps of ultrasonically recording signal generated by destruction of the microbubble.

3. A method according to claim 1 comprising the further steps of reducing the applied power intensity to less than said threshold intensity, then ultrasonically recording the reflow of said microbubble agent into the region of interest.

4. A method according to claim 1, wherein said microbubble population is comprised of microbubbles having diameters within the range of 1 to 10 microns.

5. A method according to claim 1, wherein said microbubble population comprises hollow microbubbles having a shell consisting essentially of a single layer.

6. A method according to claim 5, wherein said microbubbles comprise a biodegradable polymer.

7. A method according to claim 6, wherein said polymer is a biocompatible amphiphilic material.

8. A method according to claim 1, wherein said microbubble population comprises microbubbles having an outer shell comprising an outer layer of biologically compatible amphiphilic material and an inner layer of a biodegradable polymer.

9. A method according to claim 7 or 8, wherein said amphiphilic material comprises a protein.

10. A method according to claim 9 wherein said protein comprises collagen, gelatin, albumin, or globulin.

11. A method according to claim 6 or 8, wherein said biodegradable polymer comprises polycaprolactone, polylactide, polyglycolide, polyhydroxyvalerate, polyhydroxybutyrate, or copolymers or mixtures thereof.

12. A method according to claim 1 wherein said region of interest is the heart.

13. A method according to claim 1 wherein said region of interest is the kidney.

14. A method according to claim 1 wherein said region of interest is the liver.

15. A method according to claim 1 wherein said threshold intensity of ultrasonic power sufficient to induce rupture of said microbubbles is at a Mechanical Index of between 0.1 and 2.6.

16. An ultrasound imaging contrast agent comprising a microbubble population having a controlled fragility wherein each microbubble of said population comprises an outer shell and a hollow core, said outer shell having a wall thickness that forms a ratio with the microbubble diameter that is substantially the same as the wall thickness to diameter ratio of all other microbubbles in the population.

17. A contrast agent according to claim 16, wherein said microbubble population comprises microbubbles having diameters within the range of 1 to 10 microns.

18. A contrast agent according to claim 16, wherein said microbubble population comprises hollow microparticles having a shell consisting essentially of a single layer.

19. A contrast agent according to claim 18, wherein said microbubbles comprise a biodegradable polymer.

20. A contrast agent according to claim 19, wherein said polymer is a biocompatible amphiphilic material.

21. A contrast agent according to claim 16, wherein said microbubble population comprises microbubbles having an outer shell comprising an outer layer of biologically compatible amphiphilic material and an inner layer of a biodegradable polymer.

22. A contrast agent according to claim 20 or 21, wherein said amphiphilic material comprises a protein.

23. A contrast agent according to claim 22 wherein said protein comprises collagen, gelatin, albumin, or globulin.

24. A contrast agent according to claim 19 or 21, wherein said biodegradable polymer comprises polycaprolactone, polylactide, polyglycolide, polyhydroxyvalerate, polyhydroxybutyrate, or copolymers or mixtures thereof.

25. A contrast agent according to claim 16 wherein said ultrasound imaging contrast agent is imaged by means of ultrasound B-mode imaging methods.

26. A contrast agent according to claim 16 wherein said ultrasound imaging contrast agent is imaged by means of ultrasound doppler methods.

27. A contrast agent according to claim 16 wherein said ultrasound imaging contrast agent is imaged by means of ultrasound pulsed inversion methods.

* * * * *